US010927339B2

(12) United States Patent
Chen et al.

(10) Patent No.: US 10,927,339 B2
(45) Date of Patent: Feb. 23, 2021

(54) **MUTANT OF *BACILLUS THURINGIENSIS* AND APPLICATION THEREOF**

(71) Applicant: Industrial Technology Research Institute, Hsinchu (TW)

(72) Inventors: Chang-Chieh Chen, Taipei (TW); Ming-Der Bai, Hemei Township (TW); Shao-I Wu, Zhudong Township (TW); Hsin-Tzu Kuo, Zhubei (TW); Wen-Chang Lu, Hsinchu (TW); Hou-Peng Wan, Taoyuan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/923,465

(22) Filed: Mar. 16, 2018

(65) Prior Publication Data

US 2018/0265836 A1 Sep. 20, 2018

(30) Foreign Application Priority Data

Mar. 17, 2017 (TW) ................................ 106108901

(51) Int. Cl.
| | |
|---|---|
| *C12N 1/12* | (2006.01) |
| *C12N 1/38* | (2006.01) |
| *C12N 1/02* | (2006.01) |
| *C12N 15/75* | (2006.01) |
| *C12R 1/07* | (2006.01) |
| *C12N 1/20* | (2006.01) |

(52) U.S. Cl.
CPC ............ *C12N 1/12* (2013.01); *C12N 1/02* (2013.01); *C12N 1/20* (2013.01); *C12N 1/38* (2013.01); *C12N 15/75* (2013.01); *C12R 1/075* (2013.01)

(58) Field of Classification Search
None
See application file for complete search history.

(56) References Cited

U.S. PATENT DOCUMENTS

| | | | |
|---|---|---|---|
| 4,952,229 A | 8/1990 | Muir | |
| 8,771,981 B2 | 7/2014 | Suzuki | |
| 8,778,660 B2 | 7/2014 | Holland et al. | |
| 2008/0248953 A1 | 10/2008 | Smith et al. | |
| 2011/0020914 A1 | 1/2011 | Abou-Nemeh | |
| 2014/0283441 A1 | 9/2014 | Holland et al. | |
| 2015/0140642 A1 | 5/2015 | Ohtake et al. | |

FOREIGN PATENT DOCUMENTS

| | | |
|---|---|---|
| CN | 101531977 A | 9/2009 |
| CN | 101803600 A | 8/2010 |
| CN | 102443562 A | 5/2012 |
| CN | 102766577 A | 11/2012 |
| CN | 103045481 A | 4/2013 |
| CN | 105039237 A | 11/2015 |
| CN | 105062946 A | 11/2015 |
| TW | 201623621 A | 7/2016 |
| WO | WO 2010/083106 A1 | 7/2010 |
| WO | WO 2010/109436 A1 | 9/2010 |
| WO | WO 2013/090628 A1 | 6/2013 |
| WO | WO 2014/028521 A1 | 2/2014 |
| WO | WO 2014/145883 A1 | 9/2014 |

OTHER PUBLICATIONS

Ali et al., "Enhancement of Chlorella vulgaris Growth and Bioremediation Ability of Aquarium Wastewater Using Diazotrophs," Pakistan Journal of Biological Sciences, vol. 15, No. 16, ISSN 1028-8880, 2012, pp. 775-782 (9 pages total).
Chevanton et al., "Screening and Selection of Growth-promoting Bacteria for Dunaliella Cultures," Algal Research, vol. 2, 2013 (Available online Jun. 7, 2013), pp. 212-222.
Cho et al., "Enhancing Microalgal Biomass Productivity by Engineering a Microalgal-bacterial Community," Bioresource Technology, vol. 175, 2015 (Available online Nov. 6, 2015), pp. 578-585.
Fuentes et al., "Impact of Microalgae—Bacteria Interactions on the Production of Algal Biomass and Associated Compounds," Mar. Drugs, vol. 14, No. 100, 2016 (Published May 19, 2016), pp. 1-16.
Gonzalez et al., Increased Growth of the Microalga Chlorella vulgaris when Coimmobilized and Cocultured in Alginate Beads with the Plant-Growth-Promoting Bacterium Azospirillum brasilense, Applied and Environmental Microbiology, vol. 66, No. 4, Apr. 2000, pp. 1527-1531.
Hernandez et al., Growth Promotion of the Freshwater Microalga Chlorella Vulgaris by the Nitrogen-fixing, Plant growth-promoting Bacterium Bacillus pumilus from Arid Zone Soils, European Journal of Soil Biology, vol. 45, 2009 (Published online Sep. 29, 2008), pp. 88-93.
Huang et al., "Identification of an Algicidal Bacteria MS7 and Primary Study on Its Algicidal Activity," Oceanologia et Limnologia Sinica, vol. 44, No. 3, May 2013, pp. 632-637, with an English abstract.
Planas et al., "Stimulative Effect of Lactic Acid Bacteria in the Growth of the Microalgae Isochrysis galbana," Journal of Coastal Life Medicine, vol. 3, No. 12, 2015 (Available online Dec. 9, 2015), pp. 925-930.

(Continued)

*Primary Examiner* — Rebecca E Prouty
(74) *Attorney, Agent, or Firm* — Birch, Stewart, Kolasch & Birch, LLP (57) ABSTRACT

The present disclosure provides a new mutant of *Bacillus thuringiensis* which is deposited under Accession number DSM 32419. The present disclosure also provides a method for manufacturing a growth promoter for promoting microalgal cell growth, including: (a) inoculating a mutant of *Bacillus thuringiensis* into a culturing medium to obtain a bacterial suspension, wherein the mutant of *Bacillus thuringiensis* is deposited under Accession number DSM 32419; (b) culturing the mutant of *Bacillus thuringiensis* in the bacterial suspension at least to a stationary phase to obtain a cultured medium of the mutant of *Bacillus thuringiensis*; and (c) performing a vacuum heating procedure on the cultured medium of the mutant of *Bacillus thuringiensis* to obtain the growth promoter for promoting microalgal cell growth, wherein the growth promoter for promoting microalgal cell growth contains active substances for promoting microalgal cell growth.

19 Claims, 8 Drawing Sheets

Specification includes a Sequence Listing.

(56) References Cited

OTHER PUBLICATIONS

Xie et al. "Promotion of Microalgal Growth by Co-culturing with Cellvibrio pealriver using Xylan as Feedstock," Bioresource Technology, vol. 200, 2016 (Available online Oct. 23, 2015), pp. 1050-1054.

Zhen et al., "Application of Microbiological Preparation and Microalgae in Aquaculture," Acta Hydrobiologica Sinica, vol. 28, No. 1, Jan. 2004, pp. 85-89 (6 pages total), with an English abstract.

SEQUENCE LISTING

```
<160> NUMBER OF SEQ ID NOS: 1

<210> SEQ ID NO 1
<211> LENGTH: 1504
<212> TYPE: DNA
<213> ORGANISM: Bacillus thuringiensis

<400> SEQUENCE: 1
gatgaacgct ggcggcgtgc ctaatacatg caagtcgagc gaatggatta agagcttgct      60
cttatgaagt tagcggcgga cgggtgagta acacgtgggt aacctgccca taagactggg     120
ataactccgg gaaaccgggg ctaataccgg ataacatttt gaaccgcatg gttcgaaatt     180
gaaaggcggc ttcggctgtc acttatggat ggacccgcgt cgcattagct agttggtgag     240
gtaacggctc accaaggcaa cgatgcgtag ccgacctgag agggtgatcg gccacactgg     300
gactgagaca cggcccagac tcctacggga ggcagcagta gggaatcttc cgcaatggac     360
gaaagtctga cggagcaacg ccgcgtgagt gatgaaggct tcgggtcgt aaaactctgt      420 tgttagggaa gaacaagtgc tagttgaata agctggcacc ttgacggtac ctaaccagaa     480
agccacggct aactacgtgc cagcagccgc ggtaatacgt aggtggcaag cgttatccgg     540
aattattggg cgtaaagcgc gcgcaggtgg tttcttaagt ctgatgtgaa agcccacggc     600
tcaaccgtgg agggtcattg gaaactggga gacttgagtg cagaagagga aagtggaatt     660
ccatgtgtag cggtgaaatg cgtagagata tggaggaaca ccagtggcga aggcgacttt     720
ctggtctgta actgacactg aggcgcgaaa gcgtggggag caaacaggat tagataccct     780
ggtagtccac gccgtaaacg atgagtgcta agtgttagag ggtttccgcc ctttagtgct     840
gaagttaacg cattaagcac tccgcctggg gagtacggcc gcaaggctga aactcaaagg     900
aattgacggg ggcccgcaca agcggtggag catgtggttt aattcgaagc aacgcgaaga     960
accttaccag gtcttgacat cctctgaaaa cctagagat agggcttctc cttcgggagc    1020
agagtgacag gtggtgcatg gttgtcgtca gctcgtgtcg tgagatgttg ggttaagtcc    1080
cgcaacgagc gcaaccttg atcttagttg ccatcattaa gttgggcact ctaaggtgac    1140
tgccggtgac aaaccggagg aaggtgggga tgacgtcaaa tcatcatgcc ccttatgacc    1200
tgggctacac acgtgctaca atggacggta caaagagctg caagaccgcg aggtggagct    1260
aatctcataa aaccgttctc agttcggatt gtaggctgca actcgcctac atgaagctgg    1320
aatcgctagt aatcgcggat cagcatgccg cggtgaatac gttcccgggc cttgtacaca    1380
ccgcccgtca caccacgaga gtttgtaaca cccgaagtcg gtggggtaac cttttggag     1440 ccagccgcct aaggtgggac agatgattgg ggtgaagtcg taacaaggta gccgtatcgg    1500
aagg                                                                 1504
```

MUTANT OF *BACILLUS THURINGIENSIS* AND APPLICATION THEREOF

CROSS REFERENCE TO RELATED APPLICATION

The present application is based on, and claims priority from, Taiwan Application Serial Number 106108901, filed on Mar. 17, 2017, the disclosure of which are hereby incorporated by reference herein in its entirety.

INCORPORATION BY REFERENCE OF SEQUENCE LISTING

A sequence listing submitted as a text file via EFS-Web is incorporated herein by reference. The text file containing the sequence listing is named "0956-A25296-US_Seq_Listing.txt"; its date of creation is May 16, 2017; and its size is 2,449 bytes.

TECHNICAL FIELD

The technical field relates to a new mutant of *Bacillus thuringiensis* and application thereof.

BACKGROUND

Since microalgae can effectively use light energy, carbon dioxide and inorganic salts to synthesize protein, fat, carbohydrates and a variety of high value-added bioactive substances, microalgae culture technology can be applied to the production of biofuels, health food, food additives, feed and other chemicals.

In recent years, with the development of bio-energy technology, for some oily microalgae, because of their advantages of high oil content (about 20-60% of cell dry weight), high photosynthetic efficiency, short growth cycle, ability to grow in various regions and environments, and ability to absorb carbon dioxide from exhaust gas of factories thus achieving the benefits of carbon reductions at the same time, various countries have invested large funds to conduct research and development of microalgae-related technology.

However, the biggest bottleneck for the development of microalgal bio-energy industry is difficult to obtain microalgal biomass with a large-scale, low-cost, and high-efficiency. According to studies, the production cost of microalgal biomass is about 60% of the total cost of bio-diesel production. Hence, increasing the biomass productivity is the key technology for improving the industrial applicability of microalgae.

Therefore, a novel technique which is capable of promoting microalgal cell growth is needed.

SUMMARY

The present disclosure provides a new mutant of *Bacillus thuringiensis* which is deposited under Accession number DSM 32419.

The present disclosure also provides a method for manufacturing a growth promoter for promoting microalgal cell growth, including: (a) inoculating a mutant of *Bacillus thuringiensis* into a culturing medium to obtain a bacterial suspension, wherein the mutant of *Bacillus thuringiensis* is deposited under Accession number DSM 32419; (b) culturing the mutant of *Bacillus thuringiensis* in the bacterial suspension at least to a stationary phase to obtain a cultured medium of the mutant of *Bacillus thuringiensis*, wherein a temperature for culturing the mutant of *Bacillus thuringiensis* is about 20-40° C.; and (c) performing a vacuum heating procedure on the cultured medium of the mutant of *Bacillus thuringiensis* to obtain the growth promoter for promoting microalgal cell growth, wherein the growth promoter for promoting microalgal cell growth contains active substances for promoting microalgal cell growth, and wherein the heating temperature for the vacuum heating procedure is about 40-90° C. and the pressure of the vacuum heating procedure is about 10-400 mmHg.

The present disclosure also provides a growth promoter for promoting microalgal cell growth, which is manufactured by the above-mentioned method for manufacturing a growth promoter for promoting microalgal cell growth.

The present disclosure further provides a method for promoting microalgal cell growth, including: culturing a microalgal cell in the presence of the above-mentioned growth promoter for promoting microalgal cell growth to promote microalgal cell growth.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In one embodiment, the present disclosure provides a new mutant of *Bacillus thuringiensis*. The above-mentioned mutant of *Bacillus thuringiensis* is capable of promoting microalgal cell growth or producing active substances or metabolites for promoting microalgal cell growth.

The microalgal cell described herein may be a eukaryotic or prokaryotic unicellular or multicellular algae, has a cell wall, is capable of performing photosynthesis and can grow in an environment of freshwater or saltwater. Common microalgae include green algae, blue algae, brown algae, red algae, etc. Examples of the above-mentioned microalgal cell may include, but are not limited to, *Haematococcus pluvialis*, *Nannochloropsis* sp., *Chlorella* sp., *Tetraselmis* sp., *Isochrysis* sp. and *Dunaliella* sp.

In one embodiment, the above-mentioned microalgal cell may be *Haematococcus pluvialis*. In another embodiment, the above-mentioned microalgal cell may be *Nannochloropsis* sp. In another embodiment, the above-mentioned microalgal cell may be *Chlorella* sp. Moreover, in one embodiment, the above-mentioned microalgal cell may be *Tetraselmis* sp., and the *Tetraselmis* sp. may be *Tetraselmis chui*, but it is not limited thereto. Furthermore, in one embodiment, the above-mentioned microalgal cell may be *Isochrysis* sp., and the *Isochrysis* sp. may be *Isochrysis galbana*, but it is not limited thereto. In addition, in one embodiment, the above-mentioned microalgal cell may be *Dunaliella* sp.

In one embodiment, the mutant of *Bacillus thuringiensis* mentioned above may be a mutant which is mutated from *Bacillus thuringiensis* DSM 29807 (deposited in the German Collection of Microorganisms and Cell Cultures (DSMZ) on Dec. 11, 2014, under Accession number DSM 29807), but it is not limited thereto. The sequence of 16S rRNA gene of the mutant of *Bacillus thuringiensis* mentioned above may include a sequence with at least 95% sequence similarity to the sequence of SEQ ID NO. 1, but it is not limited thereto.

In another embodiment, the mutant of *Bacillus thuringiensis* mentioned above may be obtained by spontaneous mutation or artificial mutagenesis. In one specific embodiment, the mutant of *Bacillus thuringiensis* mentioned above is obtained by artificial transposon mutagenesis.

In one specific embodiment, the mutant of *Bacillus thuringiensis* mentioned above may be *Bacillus thuringiensis* mutant ITRI-BtM101 which is deposited in the German Collection of Microorganisms and Cell Cultures (DSMZ) on Jan. 30, 2017, under Accession number DSM 32419. The deposit will be maintained under the terms of the Budapest Treaty. This deposit is not an admission that a deposit is required under 35 U.S.C. M2. The deposit will irrevocably and without restriction or condition be available to the public upon issuance of a patent. However, it should be understood that the availability of a deposit does not constitute a license to practice the subject invention in derogation of patent rights granted by government action. The *Bacillus thuringiensis* mutant ITRI-BtM101 may be obtained by performing artificial transposon mutagenesis on *Bacillus thuringiensis* DSM 29807. Furthermore, in this specific embodiment, the sequence of 16S rRNA gene of the *Bacillus thuringiensis* mutant ITRI-BtM101 may be the sequence of SEQ ID NO. 1.

In another embodiment of the present disclosure, a method for manufacturing a growth promoter for promoting microalgal cell growth is provided.

The microalgal cell described herein may be a eukaryotic or prokaryotic unicellular or multicellular algae, has a cell wall, is capable of performing photosynthesis and can grow in an environment of freshwater or saltwater. Common microalgae include green algae, blue algae, brown algae, red algae, etc. Examples of the above-mentioned microalgal cell may include, but are not limited to, *Haematococcus pluvialis*, *Nannochloropsis* sp., *Chlorella* sp., *Tetraselmis* sp., *Isochrysis* sp. and *Dunaliella* sp.

In one embodiment, the above-mentioned microalgal cell may be *Haematococcus pluvialis*. In another embodiment, the above-mentioned microalgal cell may be *Nannochloropsis* sp. In another embodiment, the above-mentioned microalgal cell may be *Chlorella* sp. Moreover, in one embodiment, the above-mentioned microalgal cell may be *Tetraselmis* sp., and the *Tetraselmis* sp. may be *Tetraselmis chui*, but it is not limited thereto. Furthermore, in one embodiment, the above-mentioned microalgal cell may be *Isochrysis* sp., and the *Isochrysis* sp. may be *Isochrysis galbana*, but it is not limited thereto. In addition, in one embodiment, the above-mentioned microalgal cell may be *Dunaliella* sp.

The method for manufacturing a growth promoter for promoting microalgal cell growth of the present disclosure may include the following steps, but it is not limited thereto.

First, a mutant of *Bacillus thuringiensis* is inoculated into a culturing medium to obtain a bacterial suspension, and the above-mentioned mutant of *Bacillus thuringiensis* is capable of promoting microalgal cell growth or producing active substances or metabolites for promoting microalgal cell growth.

In one embodiment, the mutant of *Bacillus thuringiensis* mentioned above may be a mutant which is mutated from *Bacillus thuringiensis* DSM 29807, but it is not limited thereto. The sequence of 16S rRNA gene of the mutant of *Bacillus thuringiensis* mentioned above may include a sequence with at least 95% sequence similarity to the sequence of SEQ ID NO. 1, but it is not limited thereto.

In another embodiment, the mutant of *Bacillus thuringiensis* mentioned above may be obtained by spontaneous mutation or artificial mutagenesis. In one specific embodiment, the mutant of *Bacillus thuringiensis* mentioned above is obtained by artificial transposon mutagenesis.

In one specific embodiment, the mutant of *Bacillus thuringiensis* mentioned above may be *Bacillus thuringiensis* mutant ITRI-BtM101 which is deposited in the German Collection of Microorganisms and Cell Cultures (DSMZ) on Jan. 30, 2017, under Accession number DSM 32419. The *Bacillus thuringiensis* mutant ITRI-BtM101 may be obtained by performing artificial transposon mutagenesis on *Bacillus thuringiensis* DSM 29807. Moreover, in this specific embodiment, the sequence of 16S rRNA gene of the *Bacillus thuringiensis* mutant ITRI-BtM101 may be the sequence of SEQ ID NO. 1.

In addition, there is no specific limitation for the composition of the culturing medium. In one embodiment, the composition of the foregoing culturing medium may include peptone, yeast extract, etc., but it is not limited thereto. The concentration of the peptone in the culturing medium may be about 0.5-10 g/L, and the concentration of the yeast extract in the culturing medium may be about 0.1-5 g/L, but they are not limited thereto. In one specific embodiment, the composition of the culturing medium may comprise 5 g/L peptone and 3 g/L yeast extract.

Next, the above-mentioned mutant of *Bacillus thuringiensis* in the bacterial suspension is cultured at least to a stationary phase to obtain a cultured medium of the mutant of *Bacillus thuringiensis*. In one embodiment, when the $OD_{600}$ value of the above-mentioned bacterial suspension reaches 2.0 or more, it may be considered that the mutant of *Bacillus thuringiensis* in the bacterial suspension reaches a stationary phase. In addition, in one embodiment, culturing the mutant of *Bacillus thuringiensis* in the bacterial suspension for about 12-72 hours can make the mutant of *Bacillus thuringiensis* grow to a stationary phase. In one specific embodiment, culturing the mutant of *Bacillus thuringiensis* for about 18 hours can make the mutant of *Bacillus thuringiensis* grow to a stationary phase.

Furthermore, the temperature for culturing the above-mentioned mutant of *Bacillus thuringiensis* is about 20-40° C., but it is not limited thereto. In one embodiment, the above-mentioned mutant of *Bacillus thuringiensis* is cultured at 30° C.

After that, a vacuum heating procedure is performed on the above-mentioned cultured medium of the mutant of *Bacillus thuringiensis* to obtain the growth promoter for promoting microalgal cell growth, in which the growth promoter for promoting microalgal cell growth contains active substances for promoting microalgal cell growth.

The heating temperature for the vacuum heating procedure mentioned above may be about 40-90° C., but it is not limited thereto. In one embodiment, the heating temperature for the vacuum heating procedure mentioned above may be about 40° C., about 50° C., about 60° C., about 75° C. or about 90° C. In one specific embodiment, the heating temperature for the vacuum heating procedure mentioned above may be about 50° C. Moreover, the pressure of the vacuum heating procedure mentioned above may be about 10-400 mmHg, but it is not limited thereto. In one embodiment, the pressure of the vacuum heating procedure mentioned above may be about 10-50 mmHg, about 50-100 mmHg, about 100-200 mmHg, about 200-300 mmHg or about 300-400 mmHg. In one specific embodiment, the pressure of the vacuum heating procedure mentioned above may be about 80 mmHg.

In one embodiment, the heating temperature for the vacuum heating procedure may be about 50° C., and the pressure of the vacuum heating procedure may be about 80 mmHg.

Furthermore, in one embodiment, the method for manufacturing a growth promoter for promoting microalgal cell growth of the present disclosure further includes a step of removing the bacterial cells from the cultured medium of the mutant of *Bacillus thuringiensis* between the above-mentioned step of obtaining the cultured medium of the mutant of *Bacillus thuringiensis* and the above-mentioned step of performing the vacuum heating procedure on the cultured medium of the mutant of *Bacillus thuringiensis*.

There is no specific limitation in the way of removing the bacterial cells from the cultured medium of the mutant of *Bacillus thuringiensis*. The only requirement is that the bacterial cells can be removed from the cultured medium of the mutant of *Bacillus thuringiensis* and the composition of the cultured medium of the mutant of *Bacillus thuringiensis* is not damaged. For example, the way of removing the bacterial cells from the cultured medium of the mutant of *Bacillus thuringiensis* can be performed through centrifugation or filtration, but it is not limited thereto.

In another embodiment, the present disclosure also provides a growth promoter for promoting microalgal cell growth. The growth promoter for promoting microalgal cell growth of the present disclosure can be obtained by any of the aforementioned methods for manufacturing a growth promoter for promoting microalgal cell growth of the present disclosure.

In another embodiment, the present disclosure further provides a method for promoting microalgal cell growth. The method for promoting microalgal cell growth described herein may include the following steps, but it is not limited thereto.

First, a microalgal cell is cultured in the presence of any of the above-mentioned growth promoters for promoting microalgal cell growth of the present disclosure to promote microalgal cell growth.

The microalgal cell described herein may be a eukaryotic or prokaryotic unicellular or multicellular algae, has a cell wall, is capable of performing photosynthesis and can grow in an environment of freshwater or saltwater. Common microalgae include green algae, blue algae, brown algae, red algae, etc. Moreover, examples of the above-mentioned microalgal cell may include, but are not limited to, *Haematococcus pluvialis*, *Nannochloropsis* sp., *Chlorella* sp., *Tetraselmis* sp., *Isochrysis* sp. and *Dunaliella* sp.

In one embodiment, the above-mentioned microalgal cell may be *Haematococcus pluvialis*. In another embodiment, the above-mentioned microalgal cell may be *Nannochloropsis* sp. In another embodiment, the above-mentioned microalgal cell may be *Chlorella* sp. Moreover, in one embodiment, the above-mentioned microalgal cell may be *Tetraselmis* sp., and the *Tetraselmis* sp. may be *Tetraselmis chui*, but it is not limited thereto. Furthermore, in one embodiment, the above-mentioned microalgal cell may be *Isochrysis* sp., and the *Isochrysis* sp. may be *Isochrysis galbana*, but it is not limited thereto. In addition, in one embodiment, the above-mentioned microalgal cell may be *Dunaliella* sp.

There is no specific limitation in the way of culturing a microalgal cell in the presence of any of the above-mentioned growth promoters for promoting microalgal cell growth of the present disclosure. The only requirement is to make the microalgal cell grow in the presence of the growth promoter for promoting microalgal cell growth or make the microalgal cell contact with the growth promoter for promoting microalgal cell growth. For example, the growth promoter for promoting microalgal cell growth can be directly added to a solution or medium containing a microalgal cell and then cultured.

In one embodiment, the way of culturing a microalgal cell in the presence of any of the growth promoters mentioned above for promoting microalgal cell growth of the present disclosure may include, but is not limited to, adding the growth promoter for promoting microalgal cell growth of the present disclosure to a solution or medium containing a microalgal cell to form a mixture solution and culturing the mixture solution.

There is no specific limitation in the adding amount of the growth promoter for promoting microalgal cell growth of the present disclosure. For example, the growth promoter for promoting microalgal cell growth of the present disclosure may account for about 1-60% (v/v) of the above-mentioned mixture solution, such as 1%, 2%, 5%, 10%, 20%, 30%, 40%, 50%, 55%, 60%, but it is not limited thereto.

In one embodiment, the method for promoting microalgal cell growth of the present disclosure may raise the number of microalgal cells of at least about 5% or more. In one embodiment, the method for promoting microalgal cell growth of the present disclosure may raise the number of microalgal cell of about 50% or more.

EXAMPLES

Example 1

Acquisition of the Mutant Strain
Artificial Transposon Mutagenesis
The mutant strain of the present disclosure was obtained by performing artificial transposon mutagenesis on *Bacillus thuringiensis* (deposited in the German Collection of Microorganisms and Cell Cultures (DSMZ) on Dec. 11, 2014, under Accession number DSM 29807).

Transposon is also called "jumping gene" or "transposable element (TE)", which is a small DNA fragment capable of transferring between DNA molecules, for example, transposon is capable of transferring from plasmid DNA to chromosome. Further, the transposition behavior between genes usually results in gene mutation, thereby making cell functions altered.

The steps of the artificial transposon mutagenesis performed in this experiment are described in the following:

1. Preparation of Competent Cells

A single colony of *Bacillus thuringiensis* DSM 29807 was picked and inoculated into a LB medium, and then the single colony-containing LB medium was cultured with 150 rpm shaking at 30° C. overnight.

Next, the cultured bacterial suspension was transferred to a fresh LB medium with a ratio of 1/200, and cultured with 150 rpm shaking at 30° C. to $OD_{550}$ value of 0.2. After that, the bacterial suspension was centrifuged to collect the bacterial cells.

The obtained bacterial cells were re-suspended and washed with an electroporation buffer (400 mM sucrose, 1 mM $MgCl_2$, 7 mM phosphate buffer, pH 6.0). Furthermore, the above-mentioned washing process was performed at 4° C. and repeated twice. Thereafter, the bacterial cells were re-suspended with the above-mentioned electroporation buffer for serving as *Bacillus thuringiensis* competent cells.

2. Electroporation of Transposon Plasmid

According to the method for performing DNA transformation on *Bacillus thuringiensis* through electroporation recited in the literature (Walter Schurter et. al, 1989), electroporation of transposon plasmid was performed on *Bacillus thuringiensis* DSM 29807.

Figure 1:
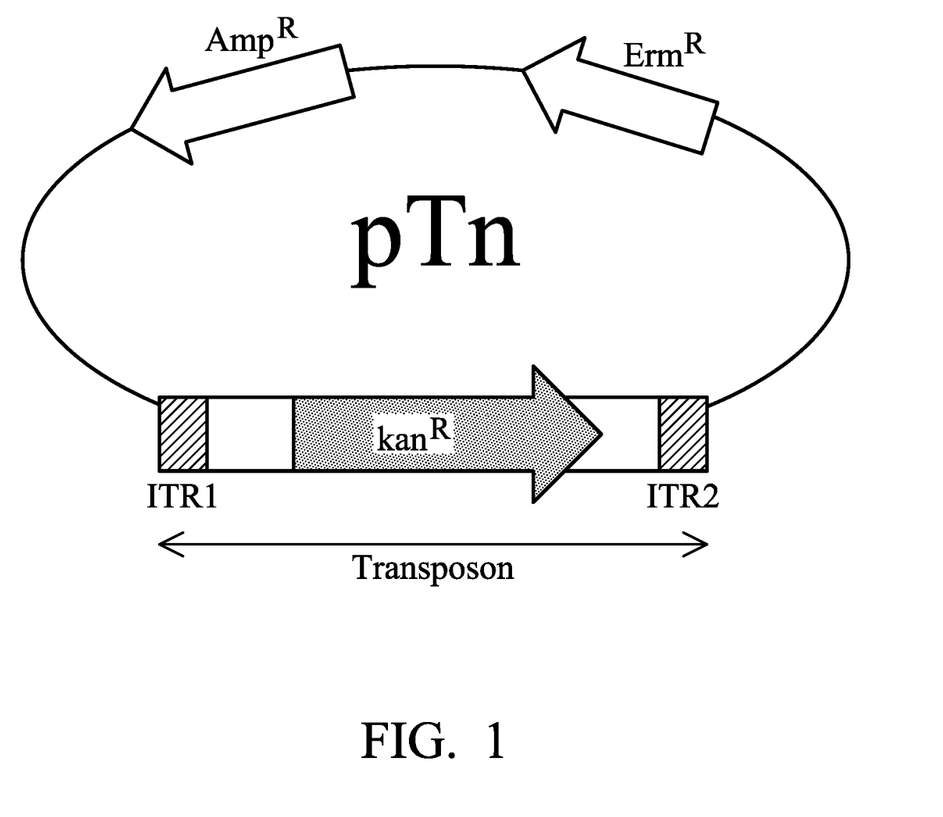
FIG. 1 shows a plasmid with a transposon used in a process in which artificial transposon mutagenesis is performed on *Bacillus thuringiensis* (deposited in the German Collection of Microorganisms and Cell Cultures (DSMZ) on Dec. 11, 2014, under Accession number DSM 29807) in one embodiment of the present disclosure.

A plasmid with transposon used in this experiment is shown in FIG. 1. The plasmid has been designed to have antibiotic resistance genes, $Amp^R$ and $Erm^R$, against ampicillin and erythromycin, respectively, and can be used to screen the bacterial strains which had been successfully transformed with the transposon plasmid. Moreover, the transposon has been designed to have an antibiotic resistance gene, $kan^R$, against kanamycin, and can be used to screen the mutant strains in which transposition has been completed.

The prepared *Bacillus thuringiensis* competent cells mentioned above was mixed with the transposon plasmid and then placed on ice for 10 minutes. Next, the mixture of the competent cells and the transposon plasmid was performed with electroporation transformation by transferring to a pre-cooled electroporation cuvette and electric pulsing with a voltage of 1.3-2.0 kV, an electric capacity of 25 µf and an electrical resistance of 100Ω. The electric pulsed mixture might contain the bacterial cells which had been successfully or unsuccessfully transformed, and be referred to "mixture of bacterial cells" hereinafter.

The mixture of bacterial cells was subsequently placed on ice for 10 minutes. Then, LB medium was added to the mixture of bacterial cells and culture with shaking was performed for bacteria repair and reproduce. After culturing for 2 hours, the mixture of bacterial cells was collected and evenly spread on a medium plate containing 5 µg/ml erythromycin, and cultured overnight to screen the bacterial cells which had been successfully transformed with the transposon plasmid.

3. Screening for Transposon Mutant Strain

Since the transposon of the transposon plasmid carries an antibiotic resistance gene ($kan^R$) against kanamycin, when transposition occurs, the transposon will move with carrying the antibiotic resistance gene ($kan^R$) against kanamycin and will insert into the genomic DNA of the bacterial strain. Then, kanamycin can be used to screen strains in which transposon mutagenesis had been successfully completed. Therefore, in order to screen transposon mutant strains, the bacterial strains which had been successfully transformed with the transposon plasmid mentioned above were spread on a medium plate containing 20 µg/ml kanamycin and cultured at 45° C. to induce transposition of the transposon and perform transposon-mediated random mutagenesis. After that, strains which could grow on a medium plate containing 20 µg/ml kanamycin and resist kanamycin but could not resist erythromycin, were the mutant strains in which transposition successfully occurred.

4. Screening for Mutant Strain that Promote Microalgal Cell Growth

Screening for mutant strain that promote microalgal cell growth was performed by using a solid culture plate containing microalgae.

First, a solid culture plate in which microalgae were evenly distributed was prepared. The method of preparing a solid culture plate in which microalgae were evenly distributed is described in the following.

Microalgae medium containing 1.5% agar was spread in a culture plate and stood to coagulate to be used as a lower layer medium. A microalgal cell suspension which was cultured to a stationary phase was mixed with the microalgae medium containing 1% agar by a ratio of 1:1 to form a soft agar, and then evenly poured on the above-mentioned lower layer medium which had coagulated to form a culture plate with double layer agar.

The culture plate with double layer agar was subsequently placed in a microalgae incubator and cultured at 25° C. with 12-hr light-dark cycle until the double layer plate presented light green, indicating that the microalgae had been able to grow on the double layer plate, and then the preparation of a solid culture plate in which microalgae were evenly distributed was completed.

After that, the mutant strains in which transposition successfully occurred were inoculated on the above-mentioned solid culture plate in which microalgae were evenly distributed. After colonies formed, the degree of green color of surroundings of each colony was observed. Among the colonies, compared to the colony of *Bacillus thuringiensis* DSM 29807, a colony whose surroundings presented deeper green was a bacterial strain capable of promoting microalgal cell growth. After the observation, it was found that compared to the colony of *Bacillus thuringiensis* DSM 29807, a colony whose surroundings presented deeper green, and thus this colony was considered as a bacterial strain capable of promoting microalgal cell growth, and the bacterial strain which formed this colony was named *Bacillus thuringiensis* ITRI-BtM101.

Moreover, the *Bacillus thuringiensis* ITRI-BtM101 had been deposited in the German Collection of Microorganisms and Cell Cultures (DSMZ) on Jan. 30, 2017, under Accession number DSM 32419.

5. Sequencing for 16S rRNA Gene

Sequencing for 16S rRNA gene was performed on *Bacillus thuringiensis* ITRI-BtM101, and the sequence of 16S rRNA gene of *Bacillus thuringiensis* ITRI-BtM101 was determined as the sequence of SEQ ID NO. 1.

Example 2

Preparation of Growth Promoter for Promoting Microalgal Cell Growth

The strain of *Bacillus thuringiensis* ITRI-BtM101 was inoculated into a culturing medium (peptone 5 g/L and yeast extract 3 g/L), and cultured at 30° C. and shaken at 150 rpm for 72 hours.

After the culturing was completed, the cultured medium was centrifuged to remove the bacterial cells and supernatant was collected.

Next, a vacuum heating procedure was performed on 300 mL of the above-mentioned supernatant, and 100 mL transparent solution was obtained as a growth promoter for promoting microalga cell growth. Conditions for the vacuum heating procedure are shown below:

Heating temperature: 50° C.;

Pressure: 80 mmHg;

Time: 2 hours.

Example 3

1. Promotion of *Haematococcus pluvialis* Growth

First, *Haematococcus pluvialis* was pre-cultured to a green cell stage by a culturing medium for *Haematococcus pluvialis*. The composition of the above-mentioned culturing medium for *Haematococcus pluvialis* is shown in Table 1, and the composition of the trace element solution in the culturing medium for *Haematococcus pluvialis* is shown in Table 2.

TABLE 1

Composition of the culturing medium for *Haematococcus pluvialis*

| Ingredient | Per liter content |
|---|---|
| $NaNO_3$ | 1.5 g |
| $K_2HPO_4$ | 0.04 g |
| $MgSO_4 \cdot 7H_2O$ | 0.075 g |
| $CaCl_2 \cdot 2H_2O$ | 0.036 g |
| Citric acid | 0.006 g |
| Ferric ammonium citrate | 0.006 g |
| EDTA (Disodium salt) | 0.001 g |
| $Na_2CO_3$ | 0.02 g |
| Trace element solution | 1.0 ml |

After being sterilized, the pH value of the culturing medium is 7.1

TABLE 2

Composition of the trace element solution of the culturing medium for *Haematococcus pluvialis* in Table 1

| Ingredients | Per liter content |
|---|---|
| $H_3BO_3$ | 2.86 g |
| $MnCl_2 \cdot 4H_2O$ | 1.81 g |
| $ZnSO_4 \cdot 7H_2O$ | 0.222 g |
| $NaMoO_4 \cdot 2H_2O$ | 0.39 g |
| $CuSO_4 \cdot 5H_2O$ | 0.079 g |
| $Co(NO_3)_2 \cdot 6H_2O$ | 49.4 mg |

In each experimental group, a different volume percent of the growth promoter (added volume of the growth promoter to total volume of experimental group) was added to prepare a medium for culturing *Haematococcus pluvialis* while in the control group, the growth promoter was replaced with sterile water. The preparations for the control group and each experimental group are shown in the following Table 3.

TABLE 3

Preparations for the control group and each experimental group

| Experimental groups | growth promoter | 10-fold concentration of the culturing medium for *Haematococcus pluvialis* | Sterile water | Total volume of the medium |
|---|---|---|---|---|
| Control group | 0 mL | 100 mL | 900 mL | 1000 mL |
| 10% growth promoter of the present disclosure | 100 mL | 100 mL | 800 mL | 1000 mL |
| 20% growth promoter of the present disclosure | 200 mL | 100 mL | 700 mL | 1000 mL |
| 30% growth promoter of the present disclosure | 300 mL | 100 mL | 600 mL | 1000 mL |

Next, after the pre-cultured microalgal suspension was centrifuged to collect the microalgae, the microalgae were inoculated to the medium of each group mentioned above and the initial concentration of the microalgae in each group was adjusted to $1 \times 10^5$ cells/mL.

The experimental groups and the control group were cultured and sampled at different time points during the incubation to count the cell numbers thereof. The above-mentioned experiment was repeated 3 times to obtain means and standard deviations of the cell number of each group at each time point.

Incubation conditions of the above-mentioned experiment are shown below:

Incubation temperature: 24° C. constant temperature;
Feeding gas: 2% $CO_2$;
Gas feeding rate: 0.2 vvm;
Stirring speed: 130 rpm;
Illumination duration: 24 hours (The illumination intensity is controlled with 16000±1000 lux for illuminated face and 2600±1000 lux for shady face)

Figure 2:
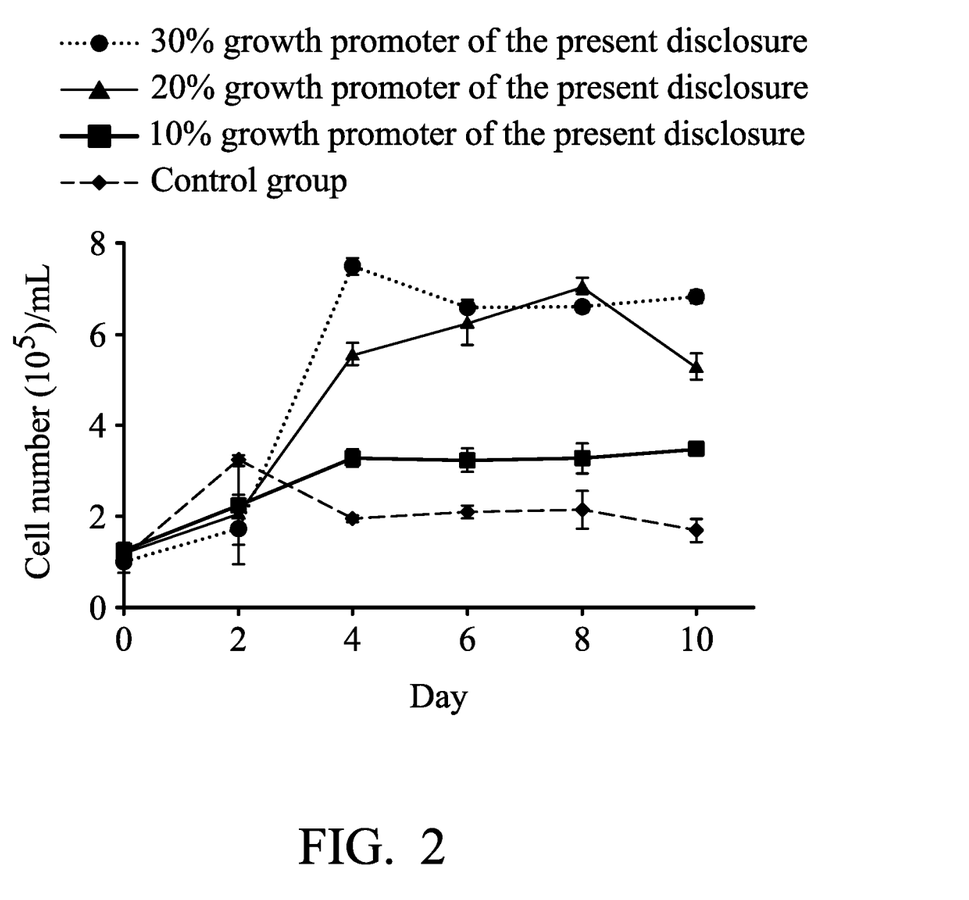
FIG. 2 shows the effect of different concentrations of the growth promoter for promoting microalgal cell growth of the present disclosure on the growth of *Haematococcus pluvialis*.

The results are shown in FIG. 2

According to FIG. 2, it is known that the growth promoter for promoting microalgal cell growth of the present disclosure can achieve the effect of promoting the growth of *Haematococcus pluvialis* by adding various volume percent (e.g., 10%, 20% and 30%) of the growth promoter. Moreover, compared to the control group, the cell numbers of *Haematococcus pluvialis* of both the experimental groups of adding 20% and 30% growth promoter was increased more than 100% on day 4 of the incubation.

2. Promotion of *Nannochloropsis* sp. Growth (1) Effect on the Growth of *Nannochloropsis* sp. which is Cultured by a Basal Medium Using Urea and Ammonium as the Main Nitrogen Sources.

The pre-cultured *Nannochloropsis* sp. suspension was added to 500 mL of culturing medium for *Nannochloropsis* sp. and $OD_{685}$ of *Nannochloropsis* sp. suspension after being inoculated was adjusted to 0.5. The composition of the above-mentioned culturing medium for *Nannochloropsis* sp. is show in Table 4.

The experimental group contained 10% growth promoter (volume of the growth promoter to total volume of the experimental group) while in the control group, the growth promoter was replaced with an equal amount of sterile water.

The experimental group and the control group were cultured and sampled at different time points during the incubation to count the cell numbers thereof. The above-mentioned experiment was repeated 3 times to obtain means and standard deviations of the cell number of each group at each time point.

Incubation conditions of the above-mentioned experiment are shown below:

Incubation temperature: 24° C. constant temperature;
Feeding gas: 2% $CO_2$;
Gas feeding rate: 1.0 vvm;
Stirring speed: 150 rpm;
Illumination duration: 24 hours (3500 lux).

TABLE 4

Composition of culturing medium for *Nannochloropsis* sp. (using urea and ammonium as the main nitrogen sources)

| Ingredients | Per liter content |
| --- | --- |
| Urea | 0.09 g |
| Ammonium sulfate | 0.06 g |
| Calcium superphosphate | 0.09 g |
| Artificial sea salt | 20 g |

Adjusting the pH value to 8.0

Figure 3A:
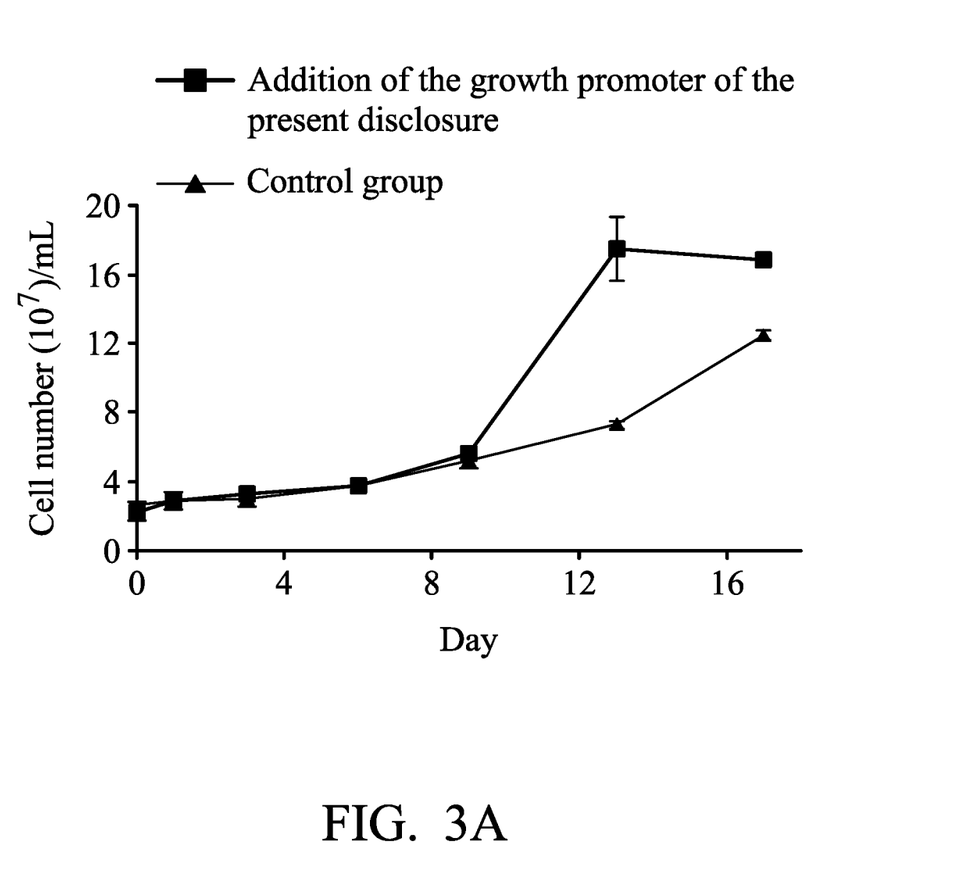
FIG. 3A shows the effect of the growth promoter for promoting microalgal cell growth of the present disclosure on the growth of *Nannochloropsis* sp. which is cultured by a basal medium using urea and ammonium as the main nitrogen sources.

The results are shown in FIG. 3A.

Base on FIG. 3A, it is known that the growth promoter for promoting microalgal cell growth of the present disclosure is capable of promoting the growth of *Nannochloropsis* sp. which is cultured by a basal medium using urea and ammonium as the main nitrogen sources.

(2) Effect on the Growth of *Nannochloropsis* sp. which is Cultured by a Basal Medium Using Nitrate as the Main Nitrogen Source.

The pre-cultured *Nannochloropsis* sp. suspension was added to 500 mL of culturing medium for *Nannochloropsis* sp. and $OD_{685}$ of *Nannochloropsis* sp. suspension after being inoculated was adjusted to 0.5. The composition of the above-mentioned culturing medium for *Nannochloropsis* sp. is show in Table 5, and the composition of the trace element solution in the culturing medium for *Nannochloropsis* sp. is shown in Table 6.

The experimental group contained 10% growth promoter (volume of the growth promoter to total volume of the experimental group) while in the control group, the growth promoter was replaced with an equal amount of sterile water.

The experimental group and the control group were cultured and sampled at different time points during the incubation to count the cell numbers thereof. The above-mentioned experiment was repeated 3 times to obtain means and standard deviations of the cell number of each group at each time point.

Incubation conditions of the above-mentioned experiment are shown below:

Incubation temperature: 24° C. constant temperature;
Feeding gas: 2% $CO_2$;
Gas feeding rate: 1.0 vvm;
Stirring speed: 150 rpm;
Illumination duration: 24 hours (3500 lux).

TABLE 5

Composition of culturing medium for *Nannochloropsis* sp. (using nitrate as the main nitrogen source)

| Ingredients | Per liter content |
| --- | --- |
| $KNO_3$ | 0.225 g |
| $NaH_2PO_4 \cdot 2H_2O$ | 0.017 g |
| Artificial sea salt | 20 g |
| Trace element solution | 3.0 ml |

Adjusting the pH value to 8.0

TABLE 6

Composition of the trace element solution of the culturing medium for *Nannochloropsis* sp. in Table 5

| Ingredients | Per liter content |
| --- | --- |
| $Na_2 EDTA \cdot 2H_2O$ | 4.4 g |
| $FeCl_3 \cdot 6H_2O$ | 3.2 g |
| $CuSO_4 \cdot 5H_2O$ | 0.01 g |
| $ZnSO_4 \cdot 7H_2O$ | 0.022 g |
| $CoCl_2 \cdot 6H_2O$ | 0.01 g |
| $MnCl_2 \cdot 4H_2O$ | 0.18 g |
| $Na_2MoO_4 \cdot 2H_2O$ | 0.006 g |

Figure 3B:
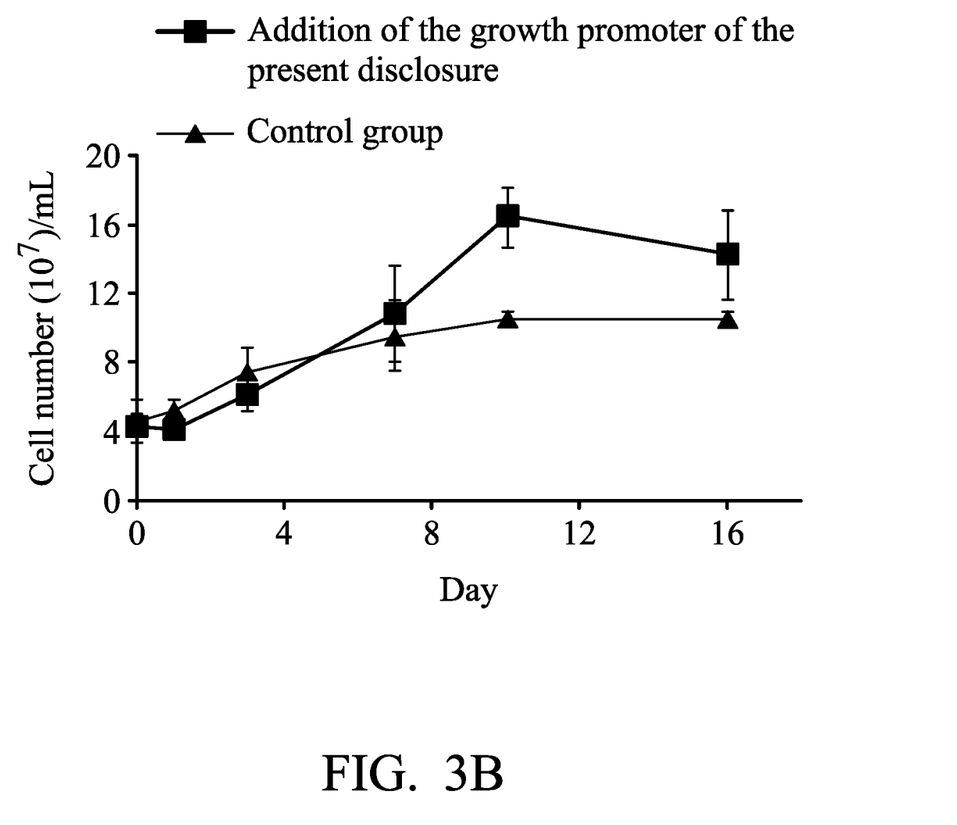
FIG. 3B shows the effect of the growth promoter for promoting microalgal cell growth of the present disclosure on the growth of *Nannochloropsis* sp. which is cultured by a basal medium using nitrate as the main nitrogen source.

The results are shown in FIG. 3B.

Based on FIG. 3B, it is known that the growth promoter for promoting microalgal cell growth of the present disclosure is capable of promoting the growth of *Nannochloropsis* sp. which is cultured by a basal medium using nitrate as the main nitrogen source.

Furthermore, based on the results of FIG. 3A and FIG. 3B, it is known that for different culturing medium for *Nannochloropsis* sp., for example the nitrogen source in the mediums are different (i.e., the nitrogen source is urea and ammonium or the nitrogen source is nitrate), the growth promoter for promoting microalgal cell growth of the present disclosure can achieve the effect of promoting the growth of *Nannochloropsis* sp.

3. Promotion of *Chlorella* sp. Growth

The pre-cultured *Chlorella* sp. suspension was added to 500 mL of culturing medium for *Chlorella* sp. and $OD_{685}$ of *Chlorella* sp. suspension after being inoculated was adjusted to 0.5. The composition of the above-mentioned culturing medium for *Chlorella* sp. is the same as the composition of the culturing medium for *Haematococcus pluvialis* shown in Table 1, and the composition of the trace element solution in the culturing medium for *Chlorella* sp. is the same as the composition of the trace element solution of the culturing medium for *Haematococcus pluvialis* shown in Table 2.

The experimental group contained 10% growth promoter (volume of the growth promoter to total volume of the experimental group) while in the control group, the growth promoter was replaced with an equal amount of sterile water.

The experimental group and the control group were cultured and sampled at different time points during the incubation to determine $OD_{685}$ values thereof. The above-mentioned experiment was repeated 3 times to obtain means and standard deviations of the $OD_{685}$ values of each group at each time point.

Incubation conditions of the above-mentioned experiment are shown below:
Incubation temperature: 24° C. constant temperature;
Feeding gas: 2% $CO_2$;
Gas feeding rate: 1.0 vvm;
Stirring speed: 150 rpm;
Illumination duration: 24 hours (10000 lux).
The results are shown in FIG. 4.

Figure 4:
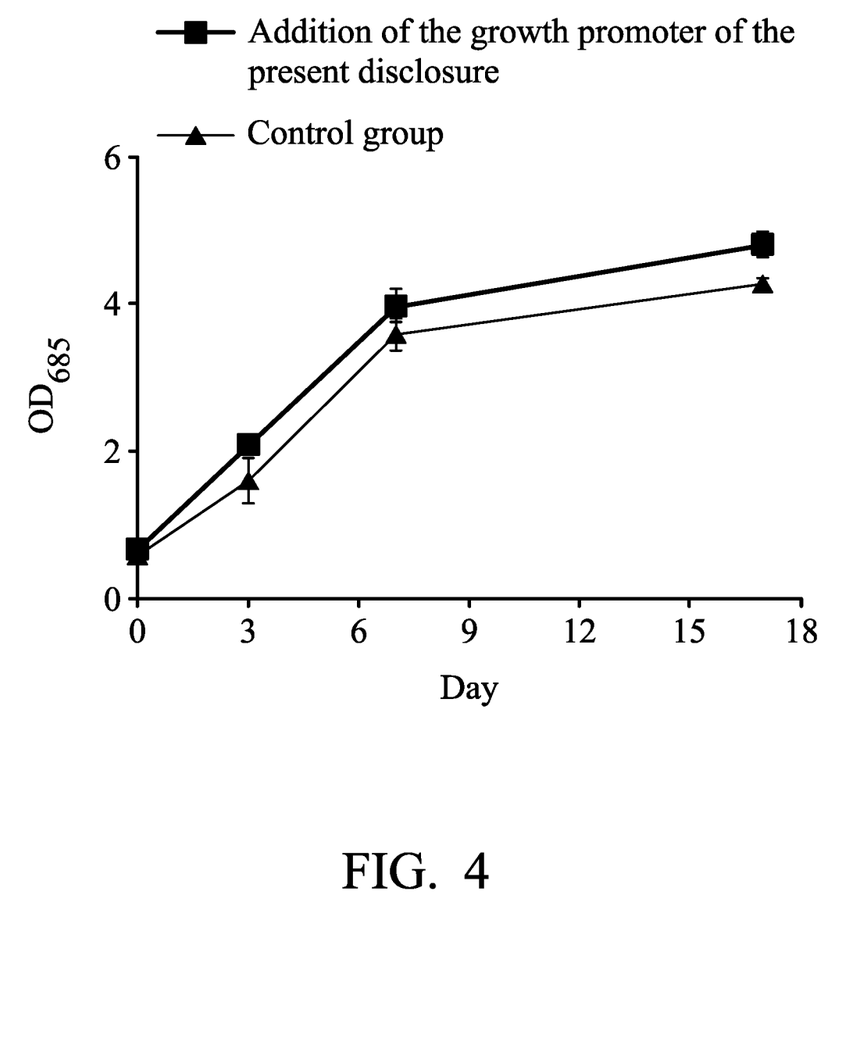
FIG. 4 shows the effect of the growth promoter for promoting microalgal cell growth of the present disclosure on the growth of *Chlorella* sp.

According to FIG. 4, the growth promoter for promoting microalgal cell growth of the present disclosure is capable of promoting the growth of *Chlorella* sp.

4. Promotion of *Tetraselmis chui* Growth

The pre-cultured *Tetraselmis chui* suspension was added to 500 mL of culturing medium for *Tetraselmis chui* and $OD_{685}$ of *Tetraselmis chui* suspension after being inoculated was adjusted to 1.0. The composition of the above-mentioned culturing medium for *Tetraselmis chui* is the same as the composition of the culturing medium for *Nannochloropsis* sp. shown in Table 5, and the composition of the trace element solution in the culturing medium for *Tetraselmis chui* is the same as the composition of the trace element solution of the culturing medium for *Nannochloropsis* sp. shown in Table 6.

The experimental group contained 5% growth promoter (volume of the growth promoter to total volume of the experimental group) while in the control group, the growth promoter was replaced with an equal amount of sterile water.

The experimental group and the control group were cultured and sampled at different time points during the incubation to determine $OD_{685}$ values thereof. The above-mentioned experiment was repeated 3 times to obtain means and standard deviations of the $OD_{685}$ values of each group at each time point.

Incubation conditions of the above-mentioned experiment are shown below:
Incubation temperature: 24° C. constant temperature;
Feeding gas: 2% $CO_2$;
Gas feeding rate: 1.0 vvm;
Stirring speed: 150 rpm;
Illumination duration: 24 hours (3500 lux)
The results are shown in FIG. 5

Figure 5:
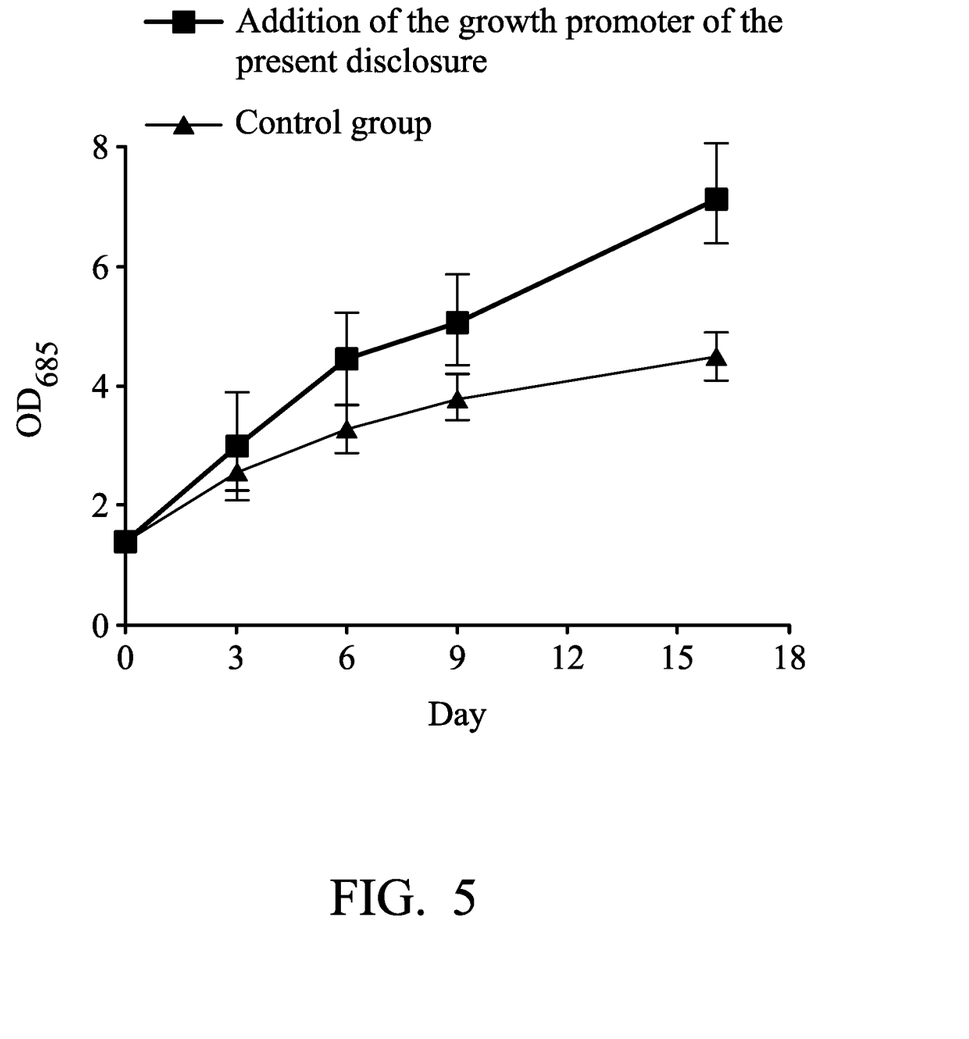
FIG. 5 shows the effect of the growth promoter for promoting microalgal cell growth of the present disclosure on the growth of *Tetraselmis chui*.

Based on FIG. 5, it is known that the growth promoter for promoting microalgal cell growth of the present disclosure is capable of promoting the growth of *Tetraselmis chui*.

5. Promotion of *Isochrysis galbana* Growth

The pre-cultured *Isochrysis galbana* suspension was added to 500 mL of culturing medium for *Isochrysis galbana* and $OD_{685}$ of *Isochrysis galbana* suspension after being inoculated was adjusted to 1.0. The composition of the above-mentioned culturing medium for *Isochrysis galbana* is the same as the composition of the culturing medium for *Nannochloropsis* sp. shown in Table 5, and the composition of the trace element solution in the culturing medium for *Isochrysis galbana* is the same as the composition of the trace element solution of the culturing medium for *Nannochloropsis* sp. shown in Table 6.

The experimental group contained 5% growth promoter (volume of the growth promoter to total volume of the experimental group) while in the control group, the growth promoter was replaced with an equal amount of sterile water.

The experimental group and the control group were cultured and sampled at different time points during the incubation to determine $OD_{685}$ values thereof. The above-mentioned experiment was repeated 3 times to obtain means and standard deviations of the $OD_{685}$ values of each group at each time point.

Incubation conditions of the above-mentioned experiment are shown below:
Incubation temperature: 24° C. constant temperature;
Feeding gas: 2% $CO_2$;
Gas feeding rate: 1.0 vvm;
Stirring speed: 150 rpm;
Illumination duration: 24 hours (3500 lux).
The results are shown in FIG. 6.

Figure 6:
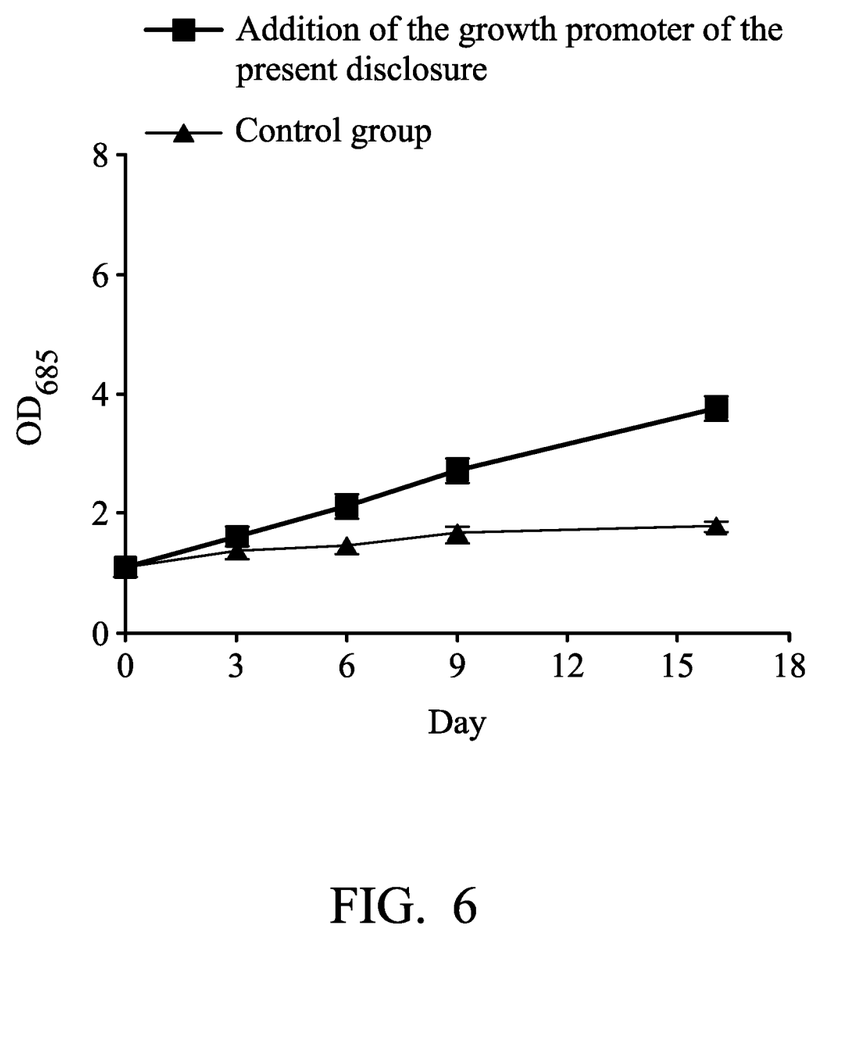
FIG. 6 shows the effect of the growth promoter for promoting microalgal cell growth of the present disclosure on the growth of *Isochrysis galbana*.

According to FIG. 6, it is known that the growth promoter for promoting microalgal cell growth of the present disclosure is capable of promoting the growth of *Isochrysis galbana*.

6. Promotion of *Dunaliella* sp. Growth

The pre-cultured *Dunaliella* sp. suspension was added to 500 mL of culturing medium for *Dunaliella* sp. and $OD_{685}$ of *Dunaliella* sp. suspension after being inoculated was adjusted to 1.0. The composition of the above-mentioned culturing medium for *Dunaliella* sp. is the same as the composition of the culturing medium for *Nannochloropsis* sp. shown in Table 5, and the composition of the trace element solution in the culturing medium for *Dunaliella* sp. is the same as the composition of the trace element solution of the culturing medium for *Nannochloropsis* sp. shown in Table 6.

The experimental group contained 5% growth promoter (volume of the growth promoter to total volume of the experimental group) while in the control group, the growth promoter was replaced with an equal amount of sterile water.

The experimental group and the control group were cultured and sampled at different time points during the incubation to determine $OD_{685}$ values thereof. The above-mentioned experiment was repeated 3 times to obtain means and standard deviations of the $OD_{685}$ values of each group at each time point.

Incubation conditions of the above-mentioned experiment are shown below:
Incubation temperature: 24° C. constant temperature;
Feeding gas: 2% $CO_2$;
Gas feeding rate: 1.0 vvm;
Stirring speed: 150 rpm;
Illumination duration: 24 hours (3500 lux).
The results are shown in FIG. 7.

Figure 7:
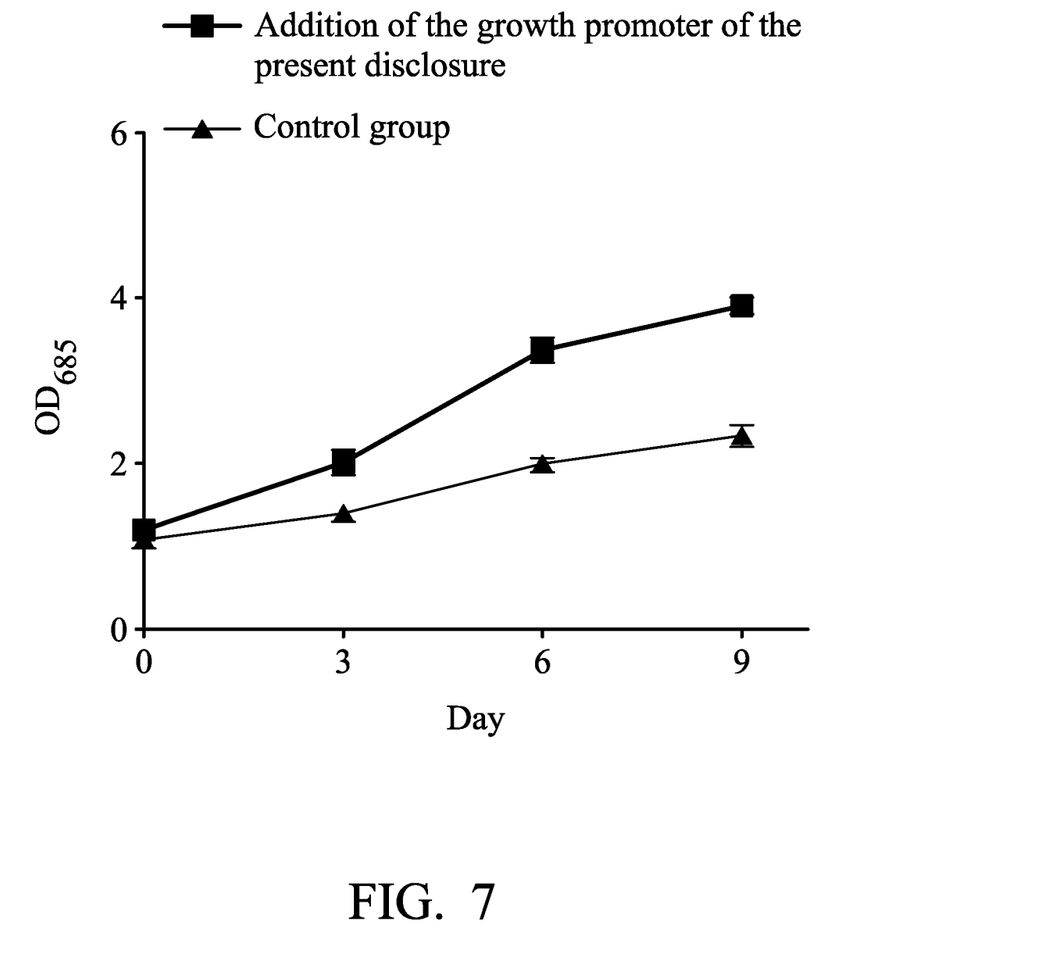
FIG. 7 shows the effect of the growth promoter for promoting microalgal cell growth of the present disclosure on the growth of *Dunaliella* sp.

According to FIG. 7, it is known that the growth promoter for promoting microalgal cell growth of the present disclosure is capable of promoting the growth of *Dunaliella* sp.

It will be apparent to those skilled in the art that various modifications and variations can be made to the disclosed embodiments. It is intended that the specification and examples be considered as exemplary only, with a true scope of the disclosure being indicated by the following claims and their equivalents.

(b) culturing the mutant of *Bacillus thuringiensis* in the bacterial suspension at least to a stationary phase to obtain a cultured medium of the mutant of *Bacillus thuringiensis*, wherein a temperature for culturing the mutant of *Bacillus thuringiensis* is ranging from 20° C. to 40° C.; and

What is claimed is:

1. A method for manufacturing a growth promoter for promoting microalgal cell growth, comprising:
    (a) inoculating a mutant of *Bacillus thuringiensis* into a culturing medium to obtain a bacterial suspension, wherein the mutant of *Bacillus thuringiensis* is deposited under Accession number DSM 32419;

(c) performing a vacuum heating procedure on the cultured medium of the mutant of *Bacillus thuringiensis* to obtain the growth promoter for promoting microalgal cell growth, wherein the growth promoter for promoting microalgal cell growth contains active substances for promoting microalgal cell growth, and wherein a heating temperature for the vacuum heating procedure is ranging from 40° C. to 50° C. and a pressure of the vacuum heating procedure is ranging from 50 mmHg to 100 mmHg.

2. The method as claimed in claim 1, further comprising a step of removing the bacterial cells from the cultured medium of the mutant of *Bacillus thuringiensis* between step (b) and step (c).

3. The method as claimed in claim 2, wherein a way for removing the bacterial cells from the cultured medium of the mutant of *Bacillus thuringiensis* comprises performing centrifugation or filtration on the cultured medium of the mutant of *Bacillus thuringiensis*.

4. The method as claimed in claim 1, wherein a composition of the culturing medium comprises peptone and yeast extract.

5. The method as claimed in claim 1, wherein the mutant of *Bacillus thuringiensis* in the bacterial suspension is cultured for 12-72 hours at least to a stationary phase.

6. The method as claimed in claim 1, wherein the heating temperature for the vacuum heating procedure is 50° C. and the pressure of the vacuum heating procedure is 80 mmHg.

7. A growth promoter for promoting microalgal cell growth, which is manufactured by the method for manufacturing a growth promoter for promoting microalgal cell growth as claimed in claim 1.

8. The growth promoter as claimed in claim 7, wherein the method further comprises a step of removing the bacterial cells from the cultured medium of the mutant of *Bacillus thuringiensis* between step (b) and step (c).

9. The growth promoter as claimed in claim 8, wherein a way for removing the bacterial cells from the cultured medium of the mutant of *Bacillus thuringiensis* comprises performing centrifugation or filtration on the cultured medium of the mutant of *Bacillus thuringiensis*.

10. The growth promoter as claimed in claim 7, wherein a composition of the culturing medium comprises peptone and yeast extract.

11. The growth promoter as claimed in claim 7, wherein the mutant of *Bacillus thuringiensis* in the bacterial suspension is cultured for 12-72 hours at least to a stationary phase.

12. The growth promoter as claimed in claim 7, wherein the heating temperature for the vacuum heating procedure is 50° C. and the pressure of the vacuum heating procedure is 80 mmHg.

13. A method for promoting microalgal cell growth, comprising:
    culturing a microalgal cell in the presence of the growth promoter for promoting microalgal cell growth as claimed in claim 7 to promote microalgal cell growth.

14. The method as claimed in claim 13, wherein a way for culturing a microalgal cell in the presence of the growth promoter for promoting microalgal cell growth comprises adding the growth promoter for promoting microalgal cell growth to a solution or medium containing a microalgal cell to form a mixture solution and culturing the mixture solution.

15. The method as claimed in claim 14, wherein the growth promoter for promoting microalgal cell growth accounts for 1-60% (v/v) of the mixture solution.

16. The method as claimed in claim 13, wherein the microalgal cell is a eukaryotic or prokaryotic unicellular or multicellular microalgae, and the microalgal cell has a cell wall and is capable of performing photosynthesis.

17. The method as claimed in claim 16, wherein the microalgal cell comprises *Haematococcus pluvialis, Nannochloropsis* sp., *Chlorella* sp., *Tetraselmis* sp., *Isochrysis* sp. or *Dunaliella* sp.

18. The method as claimed in claim 17, wherein the *Tetraselmis* sp. is *Tetraselmis* chuff.

19. The method as claimed in claim 17, wherein the *Isochrysis* sp. is *Isochrysis galbana*.

* * * * *